United States Patent [19]

Bencini et al.

[11] Patent Number: 5,866,738
[45] Date of Patent: Feb. 2, 1999

[54] PROCESS FOR THE ALKYLATION OF AROMATIC COMPOUNDS

[75] Inventors: Elena Bencini; Gino Goffredi; Eugenio Andreoli, all of Mantova, Italy

[73] Assignee: Enichem S.p.A., Milan, Italy

[21] Appl. No.: 917,181

[22] Filed: Aug. 25, 1997

Related U.S. Application Data

[63] Continuation of Ser. No. 761,339, Dec. 6, 1996, abandoned.

[30] Foreign Application Priority Data

Dec. 21, 1995 [IT] Italy .................. MI95A2704

[51] Int. Cl.$^6$ ........................................ C07C 2/66
[52] U.S. Cl. ........................................ 585/448
[58] Field of Search .................... 585/446, 448, 585/467, 468; 502/415

[56] References Cited

U.S. PATENT DOCUMENTS

| | | | |
|---|---|---|---|
| 4,358,362 | 11/1982 | Smith et al. ........................ | 208/91 |
| 4,579,723 | 4/1986 | Weltmer et al. ..................... | 423/219 |
| 5,091,358 | 2/1992 | Birbara et al. ..................... | 502/412 |
| 5,300,722 | 4/1994 | Steigelmann et al. ................ | 585/467 |

FOREIGN PATENT DOCUMENTS

| | | |
|---|---|---|
| 0 432 814 | 6/1991 | European Pat. Off. . |
| 63-264137 | 11/1988 | Japan . |
| 4198139 | 7/1992 | Japan . |
| 2 005 299 | 4/1979 | United Kingdom . |

*Primary Examiner*—Glenn Caldarola
*Assistant Examiner*—Thuan D. Dang
*Attorney, Agent, or Firm*—Oblon, Spivak, McClelland, Maier & Neustadt, P.C.

[57] ABSTRACT

Process for the alkylation of aromatic compounds which comprises contacting an olefin with an aromatic hydrocarbon in the presence of a zeolite and under conventional operating conditions, characterized in that the aromatic hydrocarbon, before the alkylation, is: a) treated to eliminate the oxygen dissolved therein; and/or b) percolated through a fixed bed consisting of particles of alumina modified with silver.

13 Claims, 1 Drawing Sheet

PROCESS FOR THE ALKYLATION OF AROMATIC COMPOUNDS

This application is a continuation of application Ser. No. 08/761.339, filed on Dec. 6, 1996, now abandoned.

BACKGROUND OF THE INVENTION

1. Field of the Invention

The present invention relates to a process for the alkylation of aromatic compounds.

More specifically, the present invention relates to a process for the alkylation of aromatic compounds, carried out in the presence of a solid catalyst, and a method for increasing the period of the catalytic activity of said catalyst.

Description of the Invention

2. Description of the Invention

The synthesis of alkylaromatic compounds is known in literature. For example, published European patent application 432.814 describes the synthesis of alkylaromatic compounds, such as cumene or ethylbenzene, by reaction between an aromatic hydrocarbon (benzene) and an olefin (propylene or ethylene) in the presence of a Beta zeolite optionally modified by the substitution of aluminium with boron, gallium or iron.

More specifically, according to this application, the reagents of the alkylation are contacted with the catalyst at a temperature between 100 and 300° C., at a pressure between 10 and 50 atms and with a flow rate of the reagents such as to give a WHSV (Weight Hourly Space Velocity) between 0.1 and 200 $h^{-1}$. Under these operating conditions, the life of the catalyst, intended as the time which passes between two regenerations, is not lengthy. This life of the catalyst however can be improved.

The Applicant has in fact found that in a process for the alkylation of aromatic compounds, it is possible to improve the life of the catalyst of the known art with particular treatment of the reagents, described hereunder, suitable for eliminating or considerably reducing the presence of poisons for the catalyst itself.

SUMMARY OF THE INVENTION

The present invention therefore relates to a process for the alkylation of aromatic compounds which comprises contacting an olefin with an aromatic hydro-carbon in the presence of a zeolite and under conventional operating conditions, characterized in that the aromatic hydrocarbon, before the alkylation, is:

a) treated to eliminate the oxygen dissolved therein; and/or b) percolated through a fixed bed consisting of particles of alumina modified with silver.

A further object of the present invention relates to a method for increasing the period of the catalytic activity of a catalyst for the alkylation of an aromatic hydrocarbon with olefins which comprises:

a) eliminating from the aromatic hydrocarbon the oxygen dissolved therein; and/or b) percolating the aromatic hydrocarbon thus treated through a filter consisting of a fixed bed of particles of alumina modified with silver.

DETAILED DESCRIPTION OF THE INVENTION

Figure 1:
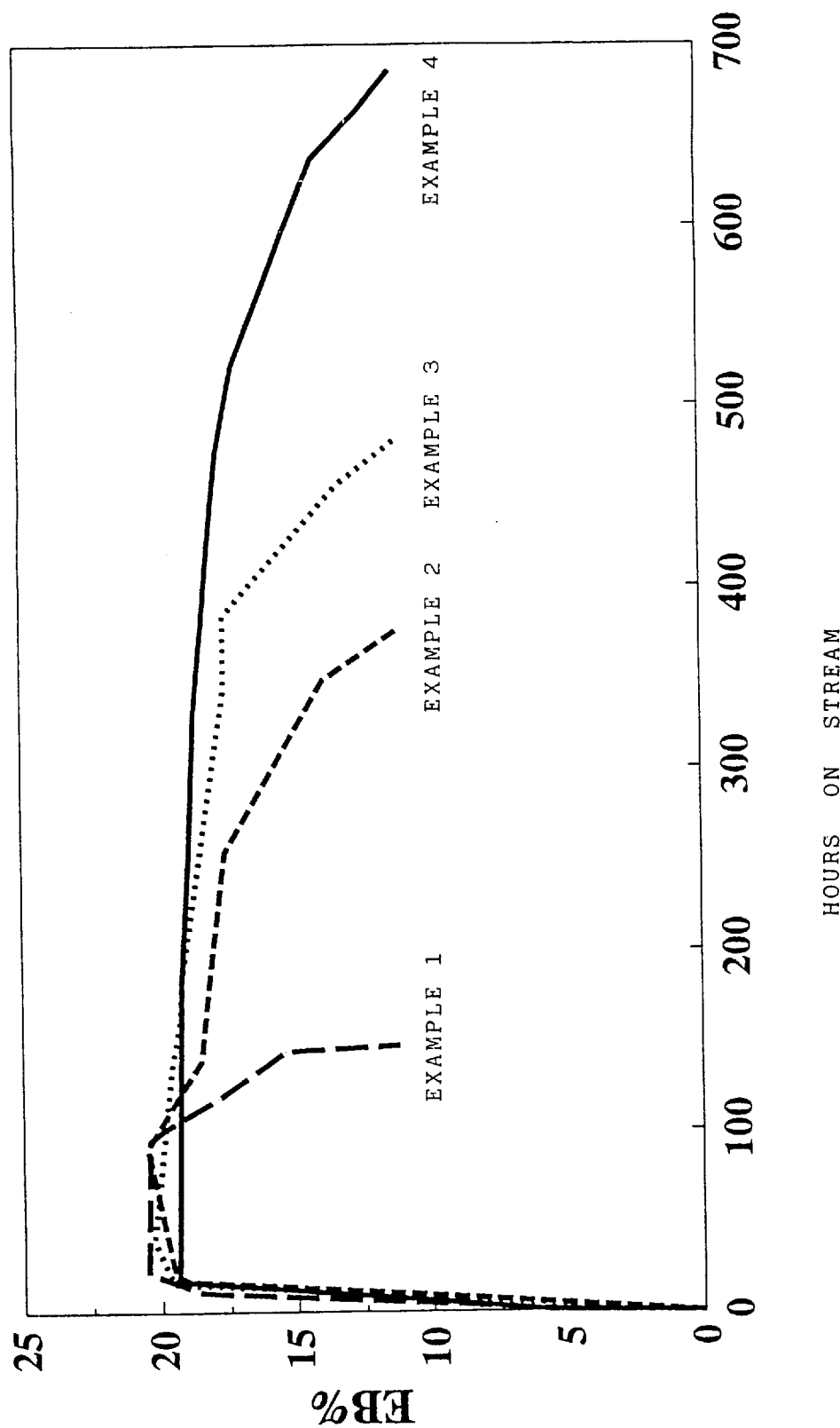
FIG. 1 is a plot of the percentage of ethyl benzene present in the effluent from the reactor versus the hours on stream, for each Examples 1–4.

The elimination of the oxygen from the aromatic hydrocarbon can be carried out with the known techniques such as distillation, also under vacuum, or stripping with inert gases, for example with nitrogen or another gas inert for the aromatic hydrocarbon.

Any aromatic hydrocarbon which can be used in the alkyation can be used in the present invention. In general, aromatic hydrocarbons liquid at room temperature, such as benzene optionally substituted with $C_1$–$C_4$ alkyl radicals, are preferred. It is also possible to use aromatic hydrocarbons containing from 10 to 25 carbon atoms, or phenols, which are solid at room temperature. In this case treatments (a) and (b) described above are carried out at such a temperature that the hydrocarbon is in the fluid state.

Similarly, any olefin which can be used in the alkylation can be used in the present invention such as, for example, $C_2$–$C_{12}$ olefins. Preferred olefins for alkylating the aromatic hydrocarbons are ethylene and propylene.

According to the present invention, the preferred treatment for eliminating the oxygen dissolved in the aromatic hydrocarbon is stripping with an inert gas, such as nitrogen. This treatment can be carried out with a semi-continuous or continuous technique. In the former case, the aromatic hydrocarbon, kept in a closed container, is flushed with a stream of nitrogen which bubbles through the liquid mass. In the latter case, the aromatic hydrocarbon is flushed with gaseous nitrogen in countercurrent using, for example, filled columns, plate-columns, etc., said columns being fed continuously at the top with the aromatic hydrocarbon and at the bottom with nitrogen in gas phase.

The treatment with nitrogen can be carried out at room temperature or at a high temperature, for example between 50 and 250° C., also depending on the physical state of the aromatic hydrocarbon, and at atmospheric pressure or a pressure slightly higher than atmospheric or under vacuum.

Whether the treatment with nitrogen is carried out in semi-continuous or in continuous, at room temperature or at a high temperature, it is preferable to operate with gas/liquid volume ratios of between 10 and 300.

The percolation on a fixed bed, following the elimination of the oxygen, is carried out through beds of alumina modified with silver. In particular, an alumina modified with 5–7% of silver can be used, having an essentially spherical form and with a particle diameter varying from 2 to 4 mm. In addition, the modified alumina has a density between 0.7 and 0.85 Kg/l and a specific surface between 100 and 200 $m^2/g$.

The alumina modified with silver according to the present invention can be prepared with the conventional techniques, for example by impregnation with silver salts and subsequent reduction of the ionic silver to metal silver.

The percolation is preferably carried out continuously, by percolating the aromatic hydrocarbon, in a gas or liquid phase, on one or more fixed beds. It is preferable to operate with liquid/solid ratios which are such as to give a WHSV between 5 and 100 $h^{-1}$ and with temperatures between 25 and 250° C.

The alkylation of the aromatic hydrocarbon with olefins is carried out with known methods, for example with the method described in published European patent application 432.814.

The alkylation of the aromatic hydrocarbon is generally carried out in liquid, gaseous or mixed phase, batchwise, in continuous or semi-continuous mode. The reaction temperature is between 100 and 300° C., preferably between 110 and 200° C., whereas the pressure is between 5 and 50 bars, preferably between 25 and 40 bars. The feeding of the reagents, if the operation is carried out in continuous or semi-continuous mode, is arranged to give a WHSV space velocity within the range of 0.1–200 h$^{-1}$. The molar ratios aromatic hydrocarbon/olefin are between 2 and 30.

Any zeolite able to provide a catalytic activity in the alkylation reaction of aromatic hydrocarbons can be used in the present invention. Examples are Y or Beta zeolites.

The Beta zeolite, described in U.S. Pat. No. 3,308,069 is preferred. This zeolite is a synthetic porous crystalline material with the following composition:

wherein x is a number less than 1, y is between 5 and 100, w is equal to 0 or is between 1 and 4, M is a metal belonging to groups IA, IIA, IIIA or is a transition metal and TEA is tetraethyl ammonium. This catalyst can also be used in a modified form by the partial substitution of the aluminium with boron, gallium or iron.

At the end of its catalytic activity the catalyst can be regenerated by thermal treatment in air at temperatures between 500 and 800° C. The time between two regenerations, thanks to the process of the present invention, is generally more than 2000–2500 hours.

Some applicative but non limiting examples are provided for a better understanding of the present invention and for its embodiment.

The Beta zeolite used in the examples was prepared according to the process described in published European patent application 432.814, having a ratio $SiO_2/Al_2O_3$ equal to 20 and a sodium content of about 200 ppm. This zeolite is in the form of microspheres having an average dimension of 8 micrometres, prepared according to the process described in published European patent application 265.018.

EXAMPLE 1 (Comparative)

6 g of Beta zeolite are charged into a pressureresistant reactor having a capacity of 0.5 litres equipped with a mechanical stirrer and electric heating systems. The reactor operates in continuous mode at a pressure of 40 bars and at a temperature of 190° C.

Benzene is fed, with a flow rate arranged to give WHSV of 17.5 h$^{-1}$, together with ethylene with a molar ratio ethylene/benzene equal to 0.2.

Downstream of the reactor the alkylated liquid and the non-reacted reagents, subjected to gaschromatographic analysis, are recovered.

The test is interrupted when the conversion of the ethylene is equal to about 60%. FIG. 1 shows the plot of the percentage of ethylbenzene present in the effluent from the reactor versus the hours on stream.

The obtained productivity is equal to 750 g of ethylbenzene per gram of active phase of catalyst.

EXAMPLE 2

The same procedure is carried out as in example 1, except that the benzene, before being fed to the reactor, is flushed with nitrogen in gaseous phase at room temperature. The volume ratio nitrogen/benzene is about 300.

FIG. 1 shows the plot of the percentage of ethylbenzene present in the effluent from the reactor versus the hours on stream.

The obtained productivity is equal to 1,750 g of ethylbenzene per gram of active phase of catalyst.

EXAMPLE 3

The same procedure is carried out as in example 1, except that the benzene, before being fed to the reactor is percolated, at 190° C. under pressure to maintain the benzene in a liquid phase, through a bed of alumina modified with about 6% by weight of silver, having a specific surface of about 175 m$^2$/g and essentially spherical particles with a diameter of 2–4 mm. The WHSV is about 12 h$^{-1}$.

FIG. 1 shows the plot of the percentage of ethylbenzene present in the effluent from the reactor versus the hours on stream.

The obtained productivity is equal to 2300 g of ethylbenzene per gram of active phase of catalyst.

EXAMPLE 4

The same procedure is carried out in example 1, except that the benzene, before being fed to the reactor, is subjected to both treatments of examples 2 and 3.

FIG. 1 shows the plot of the percentage of ethylbenzene present in the effluent from the reactor versus the hours on stream.

The obtained productivity is equal to 3250 g of ethylbenzene per gram of active phase of catalyst.

We claim:

1. A process for the alkylation of aromatic compounds which comprises contacting an olefin with an aromatic hydrocarbon in the presence of a zeolite wherein the aromatic hydrocarbon, before the alkylation, is:

a) optionally treated to eliminate oxygen dissolved therein; and b) percolated through a fixed bed consisting of particles of alumina modified with silver metal.

2. The process according to claim 1, wherein the elimination of the oxygen from the aromatic hydrocarbon is carried out by distillation or by stripping with inert gases.

3. The process according to claim 1 wherein the aromatic hydrocarbon is benzene optionally substituted with $C_1$–$C_4$ alkyl radicals.

4. The process according claim 1, wherein the olefins used to alkylate the aromatic hydrocarbons are ethylene and propylene.

5. The process according to claim 2, wherein the elimination of the oxygen dissolved in the aromatic hydrocarbon is carried out by stripping with nitrogen.

6. The process according to claim 5, wherein the stripping treatment with nitrogen is carried out at room temperature or at temperatures of between 50 and 250° C.

7. The process according to claim 5 or 6, wherein the treatment with nitrogen is carried out with volume ratios gas/liquid of between 10 and 300.

8. The process according to claim 5, wherein the percolation, following the treatment with nitrogen, is carried out through beds of alumina modified with 5–7% by weight of silver metal.

9. The process according to claim 1, wherein the alumina modified with silver consists of particles having a diameter between 2 and 4 mm.

10. The process according to claim 1, wherein the modified alumina has a density between 0.7 and 0.85 Kg/l and a specific surface between 100 and 200 m$^2$/g.

11. The process according to claim 1, wherein the percolation operation is carried out with WHSV between 5 and 100 h$^{-1}$.

12. The process according to claim 1, wherein the percolation operation is carried out at temperatures between 25° and 250° C.

13. A method for increasing the period of the catalytic activity of a catalyst for the alkylation of an aromatic hydrocarbon with with olefins which comprises:

a) optionally eliminating from the aromatic hydrocarbon oxygen dissolved therein; and b) percolating the aromatic hydrocarbon through a filter consisting of a fixed bed of particles of alumina modified with silver metal.

* * * * *